United States Patent [19]
Pedersen et al.

[11] Patent Number: 5,342,768
[45] Date of Patent: Aug. 30, 1994

[54] IMMOBILIZATION OF THERMOSTABLE MICROBIAL LIPASE BY ADSORPTION TO MACROPOROUS INORGANIC CARRIER PARTICLES

[75] Inventors: Sven Pedersen, Gentofte; Tomas T. Hansen, Allerod, both of Denmark

[73] Assignee: Novo Nordisk A/S, Bagsvaerd, Denmark

[21] Appl. No.: 678,342

[22] PCT Filed: Nov. 15, 1989

[86] PCT No.: PCT/DK89/00270

§ 371 Date: Apr. 24, 1991

§ 102(e) Date: Apr. 24, 1991

[87] PCT Pub. No.: WO90/05778

PCT Pub. Date: May 31, 1990

[30] Foreign Application Priority Data

Nov. 16, 1988 [DK] Denmark .............................. 6386/88

[51] Int. Cl.$^5$ ......................... C12P 7/64; C12P 7/62; C12N 11/14
[52] U.S. Cl. ................................... 435/134; 435/135; 435/176
[58] Field of Search ............... 435/134, 135, 176, 180

[56] References Cited

U.S. PATENT DOCUMENTS 4,472,503  9/1984  Matsuo et al. ...................... 435/176
4,798,793  1/1989  Eigtved ............................ 435/180 X

FOREIGN PATENT DOCUMENTS

WO85/00380  1/1985  PCT Int'l Appl. .
WO88/02775  4/1988  PCT Int'l Appl. .

OTHER PUBLICATIONS

Lavayre et al., Biotechnology and Bioengineering, vol. 24, pp. 1007-1013 (1982).
Artyomova et al., Advances in Colloid and Interface Science, vol. 25, pp. 235-248 (1986).

*Primary Examiner*—David M. Naff
*Attorney, Agent, or Firm*—Steve T. Zelson; Cheryl H. Agris

[57] ABSTRACT

A particulate immobilized microbial lipase is prepared by adsorption of lipase to macroporous inorganic carrier particles having specific characteristics. The carrier particles contain at least 65% silica or silicates, an excess of 90% particles having a size between 100 and 1000 μm and an excess of 80% pores exhibiting a diameter of between 12 and 45 times the diameter of a lipase molecule. The lipase is adsorbed to the carrier particles by contacting the particles with an aqueous solution of lipase and drying the particles to a water content between 1 and 20%. The lipase is preferably a thermostable lipase from a *Humicola* species, *Candida antarctica* or *Rhizomucor miehei*. The particulate immobilized lipase is cheap to produce, exhibits a high specific activity, and can be used for interesterification of fats, hydrolysis of fats or synthesis of fatty acid esters.

18 Claims, 2 Drawing Sheets

IMMOBILIZATION OF THERMOSTABLE MICROBIAL LIPASE BY ADSORPTION TO MACROPOROUS INORGANIC CARRIER PARTICLES

BACKGROUND OF THE INVENTION

Extensive research activities have been directed in order to provide immobilized lipase preparation, in consideration of the growing use for immobilized lipases to interesterification. Some of the first industrially applicable immobilized lipase preparations for interesterification are described in U.S. Pat. No. 4,275,081, col. 7, lines 28-35, from which it appears that the immobilized lipase preparations are prepared by acetone precipitation of an aqueous lipase solution on Celite ® diatomaceous earth.

However, the half life of these immobilized lipase preparations are relatively low. Also, the obtainable specific lipase activity is relatively low. Furthermore, a dust problem during storage and loading into the columns is present, and also, solvents are necessary during use of these prior art immobilized lipase preparations.

Thus, the research activities have more or less been focused on immobilization of lipase on carriers with hydrophobic binding sites. Reference can be made to Biotechnology and Bioengineering, Vol. XXIV, pp. 1007-1013 (1982), from which it appears that it is generally assumed that in the preparation of immobilized lipase preparations with high half life and high activity for industrial applications a carrier with hydrophobic binding sites more or less was a conditio sine qua non. Also, reference is made to published Danish patent No. 152763, which describes an immobilized lipase preparation with a carrier consisting of a particulate macroporous weak anion exchange resin, e.g. a resin belonging to the Duolite ® series. Carrier resins of this kind have hydrophobic binding sites, and the preparations exhibit a high half life and are very well suited for industrial interesterification.

Even so, however, these anion exchange resins do have drawbacks. In the first place they are very expensive, and this has a great bearing on the price of the immobilized lipase preparations. In the second place it has been found that during use in organic media extractables from the anion exchange resins are transferred to the organic medium, and even if the amount of the extractables is low, this often represents a serious disadvantage, especially if the end product of the enzymatic process is intended for human consumption. It is possible to wash the resins with organic solvents prior to immobilization, but this is a costly step.

Thus, a need exists for a cheap immobilized lipase preparation with high half life and possibility of high specific activity and without any possibility for transfer of extractables from the carrier to an organic phase.

SUMMARY OF THE INVENTION

Now, according to the invention it has been found that the above need can be fulfilled if—against the prejudice in regard to the above indicated diatomaceous earth carrier—a carefully defined class of inorganic carriers is used.

Thus, the particulate immobilized lipase according to the invention with macroporous silica or silicates as a carrier material is characterized by the fact that more than 90% of the particles have particle sizes between 100 and 1000 μm, wherein more than 80% of the pores in the particles exhibit a diameter between 10 and 45 times the diameter of the lipase globules, and wherein the water content of the particulate immobilized lipase is between 1 and 20%, preferably between 2 and 20%, more preferably between 5 and 20%.

From an article in Advances in Colloid and Interface Science, 25 (1986) 235-248, "Macroporous Silica in Chromatography and Immobilization of Biopolymers" it appears that the maximum capacity for the immobilization of enzymes is found with silicas having average pore sizes of 5 to 10 times the size of the protein globules. Suprisingly, we have found that the maximum capacity for the immobilization of lipases appears with silicas or silicates with pore sizes between 10 and 45 times the size of the lipase globules. This article does not focus on lipase at all, but is concerned with enzymes in general, even with proteins in general. The invention is exclusively directed to particulate immobilized lipases, and lipases are quite extraordinary enzymes in the sense that the enzymatic activity is functioning on an interface between two phases, meaning that the immobilization of the lipases is a very delicate problem, which highly limits the utility of known immobilization techniques in the field comprising lipase immobilization, vide J. lavayre et al., Preparation and Properties of Immobilized Lipases, Biotechnology and Bioengineering, vol. XXIV, pp. 1007-1013 (1982), John Wiley & Sons.

The term "macroporous" means that the pores are at least 250 Å in diameter. The pore diameter is measured by means of the B.E.T. method.

The carrier material used in the immobilized lipase according to the invention consists of at least 65% weight of silica and/or silicates, preferably at least 90% by weight of silica and/or silicates. Also, in this specification with claims "silica or silicates" means genuine silica or silicates, i.e. silica or silicates, which are not derivatized.

The diameter of the lipase globules can be measured by means of X-ray diffraction analysis and other methods, as indicated in "Biochemistry" of Albert L. Lehninger, 1970, Worth Publishers Inc., page 142-143.

The diameter of the lipase globules is generally around 50 Å. thus, the particulate silica gels described in the Grace information leaflet SG BC 1E/June 1987 (from Grace, Grace Plaza, 1114 Avenue of the Americas, New York, N.Y. 10036-7794) are well suited for the purpose of the invention, as most of them have pore diameters of 500 Å or above. Even if it is indicated in the information leaflet that the silica gels can be used for immobilization of cells and enzymes, there is no indication in the leaflet whatsoever that the silica gels can be used for immobilization of lipases, and lipases are exceptional enzymes which in comparison to other enzymes exhibit unique characteristics in regard to immobilization, as explained earlier in this specification.

It has been found that the inorganic powder used in the previously cited U.S. Pat. No. 4,275,081 (col. 12, line 48) cannot be used in the method according to the invention (vide the particle size limitation in claim 1), and that acetone precipitation with all the accompanying disadvantages seems to be the only way to fix the lipase on the Celite ® powder used in U.S. Pat. No. 4,275,081.

Also, from the previously cited article in Biotechnology and Bioengineering, Vol. XXIV, pp. 1007-1013 (1982) it appears that lipases can be immobilized on a Sphaerosil ® support which is derivatized by introduction of iodopropyl groups and which is a hydrophobic porous support with a pore diameter of 1250–3000 Å. However, Sphaerosil is extremely expensive. One of the most important aspects in regard to the particulate immobilized lipase according to the invention is the possibility for production of a cheap particulate immobilized lipase preparation, in relation to which derivatization of the carrier is unnecessary.

In EP patent No. 147,914 is described an immobilized lipase preparation on which lipase is immobilized on a glass carrier with particle size 30–45 mesh and an average pore size of 400 Å. However, it also appears from EP patent No. 147,914 that it is imperative that a coupling agent of the organotitanate type is used for the production of the immobilized lipase preparation.

In Applied Microbiol. Biotechnol. 28, p. 527–30 is described a lipase preparation which is immobilized on a glass carrier PG 700–80 with a particle size of 20–80 mesh and a pore diameter of 700 Å. However, from page 528 it appears that the water was totally removed, and this places the known immobilized lipase preparation outside the scope of this invention, because the immobilized lipase according to the invention contains 1–20% of water. This difference has the consequence that the performance of the known product is inferior to the performance of the immobilized lipase according to the invention.

From a paper in Enzyme Microbial Technology, 1984, Vol. 6, October, 443–446 it appears that different grades of diatomaceous earth can be used as supports for an immobilized lipase intended as an agent for enzymatic interesterification of fats. However, these supports have pore sizes far bigger than the pore sizes of the carrier material of the particulate immobilized lipase according to the invention. This means that the activity for each introduced LU is considerably less than in relation to the invention, due to the considerably smaller specific surface area of the known immobilized lipase. Thus, in relation to the known immobilized lipase preparation a multilayer of lipase is present on the carrier, whereas in relation to the immobilized lipase according to the invention a monolayer of lipase is present on the carrier.

DESCRIPTION OF THE PREFERRED EMBODIMENTS

Figure 1:
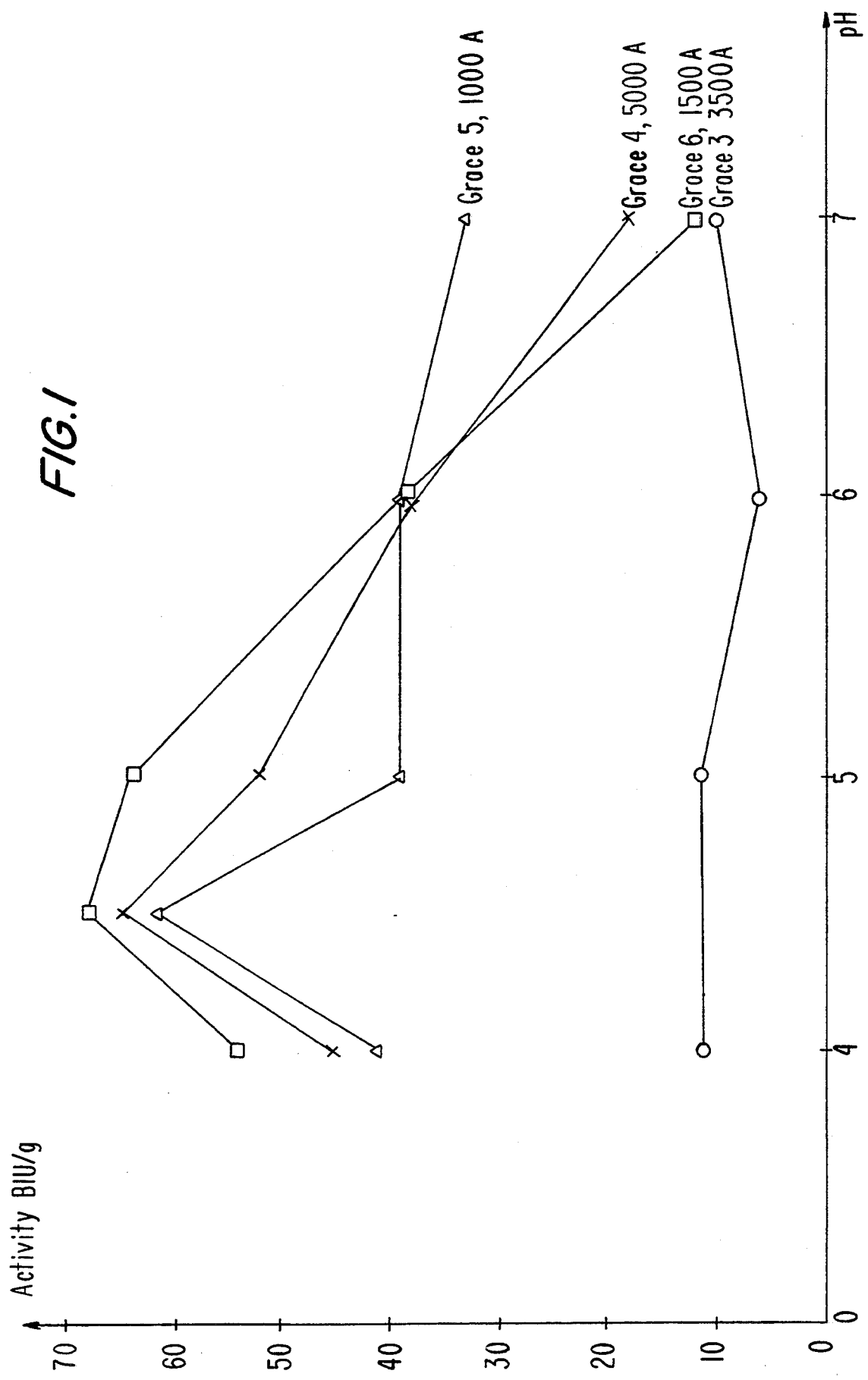
FIG. 1 illustrates the dependency between expressed lipase activity (BIU/g) and pH during loading of a lipase on carrier materials with different pore sizes.

In a preferred embodiment of the immobilized lipase according to the invention more than 90% of the particles have sizes between 200 and 800 $\mu$m, preferably between 200 and 400 $\mu$m. If the particle size is below 200 $\mu$m, the pressure loss in a column will tend to be too large, and if the particle size is above 800 $\mu$m, the diffusion inhibition tends to be too high.

In a preferred embodiment of the immobilized lipase according to the invention more than 80% of the pores in the particles exhibit a diameter between 12 and 40 times the diameter of the lipase globules. In this interval of pore sizes the expressed lipase activity, measured in BIU/g, is especially high.

In a preferred embodiment of the immobilized lipase according to the invention the lipase is a thermostable lipase. In this manner the immobilized lipase can be used in columns operating with high temperature, whereby at least two advantages are obtainable: in the first place it is possible to use the immobilized lipase, e.g. for interesterification, without a solvent, due to the relatively low viscosity of the reaction mixture, in the second place the reaction rate will be relatively high, and in the third place the diffusion rate of substrate and products inside the pores will be increased.

In a preferred embodiment of the immobilized lipase according to the invention the lipase is produced by cultivation of a microorganism containing a gene encoding for and expressing a lipase derived from a strain of Humicola species, *Candida antarctica* or *Rhizomucor miehei*. These lipases have been tested, and they all perform well at high temperature in a column.

Also the invention comprises a method for production of a particulate immobilized lipase according to the invention, wherein an aqueous solution of a microbial lipase is contacted with a particulate carrier material, which is macroporous silica or silicates, in which more than 90% of the particles have sizes between 100 and 1000 $\mu$m, and in which more than 80% of the pores in the particles exhibit a diameter between 10 and 45 times the diameter of the lipase globules, during a period of time sufficient to bind the wanted amount of lipase to the carrier material, whereafter the thus formed particulate immobilized lipase is separated from the aqueous phase and the separated immobilized lipase is dried to a water content of between approximately 2 and 20%. It has been found that a wash of the particulate immobilized lipase between the separation thereof from the aqueous phase and the drying thereof is advantageous.

The period of time which is sufficient to bind the wanted amount of lipase to the carrier material varies from lipase to lipase, and it can range between a few minutes and a few days.

In a preferred embodiment of the method according to the invention the proportion between the amount of the aqueous solution of the microbial lipase and the weight of carrier material corresponds to 10,000–500,000 LU/g of carrier material (dry weight). If the loading is less than 10,000 LU/g of carrier material the velocity of the liquid reaction mixture through the column tends to be too little, and it is very difficult to obtain a loading above 500,000 LU/g of carrier material.

In a preferred embodiment of the method according to the invention the pH during contact between carrier material and aqueous solution does not deviate more than 1 pH unit from the optimal loading pH of the lipase in question in regard to expressed lipase activity. Thereby the expressed lipase activity, measured in BIU/g of immobilized lipase, is as large as possible. Reference can be made to FIG. 1, which will be explained in more detail in the following.

In a preferred embodiment of the method according to the invention the separation is performed by simple filtration. This is the simplest and cheapest way of performing the separation.

Also the invention comprises a use of the immobilized lipase according to the invention. The use comprises a method for interesterification of fats, wherein liquid fats or fatty mixtures, including free fatty acids or fatty acid esters, are contacted with the immobilized lipase preparation according to the invention, a method for hydrolysis of fats, wherein triglycerides and water are contacted with the immobilized lipase preparation according to the invention, and a method for synthesis of glycerides or other fatty acid esters, wherein a mixture of glycerol or substituted glycerols or other types of alcohols and free fatty acids is contacted with the immobilized lipase preparation according to the invention. In relation to these uses no solvent is necessary but a solvent can be used, if desired. Also, the uses may be carried out continuously, e.g. in columns, or batchwise.

The lipase activity unit (LU) is determined as described in the publication AF 95.1/2.GB of 83-01-03, obtainable from Novo-Nordisk A/S, Novo Alle, DK-2880 Bagsvaerd, Denmark.

The lipase activity expressed in BIU (Batch Interesterification Units) is determined as described in the publication AF 206-2, obtainable from Novo-Nordisk A/S, Novo Alle, DK-2880 Bagsvaerd, Denmark.

The data on FIG. 1 originated as follows. The silica carrier which is a carrier product from Grace described in Biocatalyst Supports SG BC 1E/June 1987 is washed with buffer at the pH to be used during the following lipase adsorption step, i.e. at pH 4, 4.5, 5, 6 and 7, vide FIG. 1, for half an hour and filtered. The wanted amount of lipase which is the lipase activity sufficient for generation of a loading of 186.000 LU/g is dissolved in 5 ml of deionized water and added to 1 g of carrier. The lipase is produced as indicated in Example 1 in Danish patent application no. 4417/86, i.e. by means of *Humicola lanuginosa*. The pH value is adjusted and the carrier and the lipase solution is slowly agitated by rotation for two hours followed by vacuum filtration. The filtrate is analyzed for hydrolytic activity (LU/ml) in order to determine the amount of adsorbed (loaded) lipase. The immobilized lipase is air dried, the moisture content is adjusted to 10% by weight, and the sample is analyzed for batch interesterification activity (BIU/g). It clearly appears from the figure that the silica carrier with pore size 1500 Å (i.e. 25 times the diameter of the lipase globules), i.e. inside the claimed interval for pore sizes) exhibits an excellent expressed lipase activity at the optimum pH.

Figure 2:
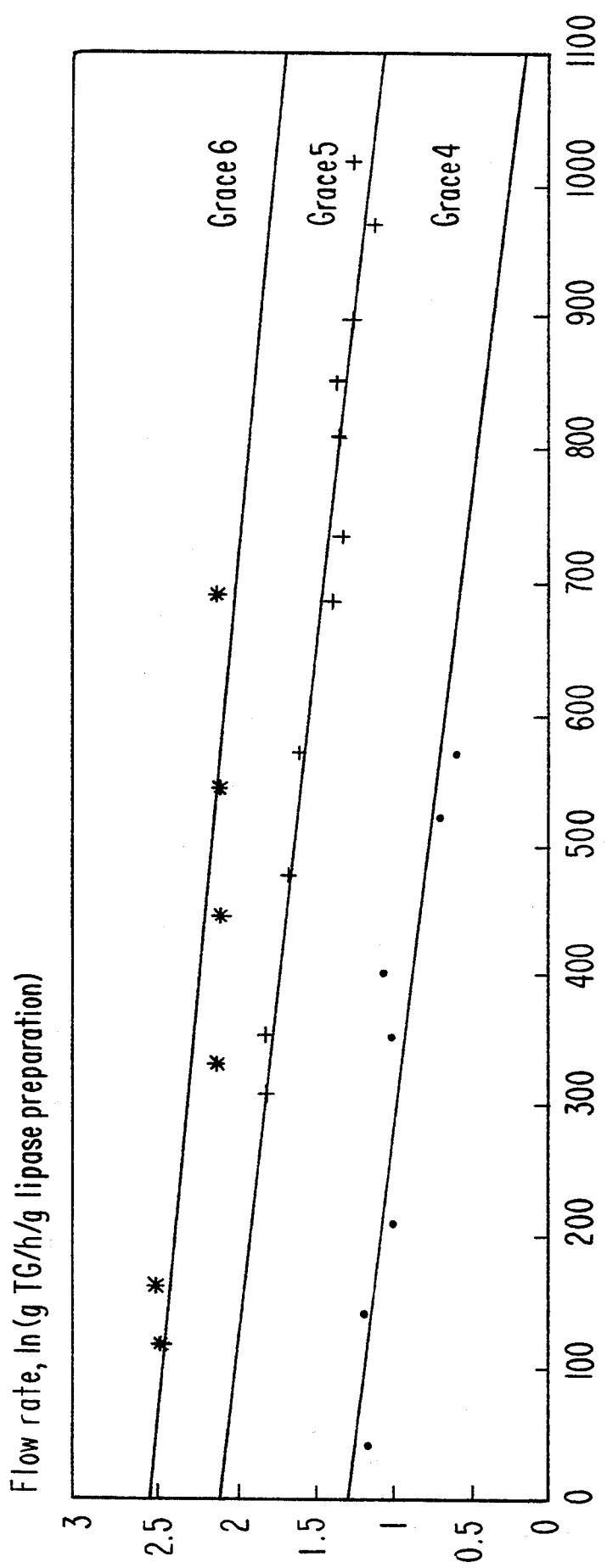
FIG. 2 shows the logarithm to the flow rate versus time for a lipase on carrier materials with different pore sizes.

On FIG. 2 the three of the four immobilized lipase preparations from FIG. 1 which are inside the scope of the present invention were tested in a column in the following manner.

A system consisting of a precolumn containing ion exchange resin saturated with water and an enzyme column (containing 4.5 g immobilized lipase preparation) in series was set up. The function of the precolumn was saturation of the substrate with water. An oil mixture consisting of 28.6% (w/w) lauric acid and 71.4% (w/w) soy bean oil was pumped through the columns. The temperature in the columns was kept at 60° C. The flow rate was adjusted in order to keep a constant conversion of 14% incorporated lauric acid in the soy bean oil. Samples were taken 3–5 times per week and analyzed by removing the free fatty acids and partial glycerides by column chromatography and methylating the triglycerides followed by capillary gas chromatography of the methyl esters. The flow rate, which is proportional to the activity, was then plotted against time when the conversion was 14%±1% incorporated lauric acid.

From the figure the following half life and initial activities can be estimated:

| Type of carrier | Initial flow rate (activity) (g TG/h/g lipase preparation | Half life hours |
|---|---|---|
| GRACE 4 | 3.6 | 700 |
| GRACE 5 | 8.0 | 750 |
| GRACE 6 | 12.7 | 850 |

TG is an abbreviation for triglyceride.

Also in this case the silica carrier with pore size 1500 Å performs very well in regard to initial flow rate.

In order to demonstrate the significance of varying water contents in the immobilized lipase preparation the following experiments were performed. Immobilized lipase preparations were prepared with Grace 6 as the carrier. The lipase was the *Humicola lanuginosa* lipase. Except for the drying the immobilized preparations were prepared as indicated in relation to FIG. 1, at pH 4.5.

The following activities were found:

| % of water | Activity | |
|---|---|---|
| | BIU/g | % of maximum |
| 0 | 15 | 29 |
| 0.5 | 24 | 47 |
| 1 | 35 | 69 |
| 2 | 48 | 94 |
| 5 | 48 | 94 |
| 10 | 51 | 100 |
| 12 | 50 | 98 |
| 15 | 49 | 96 |
| 20 | 46 | 90 |

The following examples further illustrate the immobilized lipase according to the invention. Example 1, 2, and 7 are production examples; Example 3, 4, 5, and 6 are application examples, and Example 8 is a comparison example.

EXAMPLE 1

2 g of carrier (Grace, pore diameter 700 Å, particle size 0.5–1 mm) was washed in 0.2M acetate buffer of pH 4.5 for half an hour and vacuum filtered. 400,000 LU (0.17 g of *Rhizomucor miehei* lipase produced as indicated in EP 238,023 and with an activity of $2.4 \times 10^6$ LU/g) was dissolved in 8 g of deionized water and added to the carrier. The pH value was adjusted to 4.5 and the slurry of carrier and enzyme solution was slowly agitated by rotation for two hours at room temperature, followed by vacuum filtration. The filtrate contained $2.7 \times 10^5$ LU corresponding to an adsorption of 32%. The immobilized lipase was dried in a vacuum oven at 25° C. overnight and the moisture content was adjusted to 10%. The sample was analyzed to 26 BIU/g.

EXAMPLE 2

1 g of carrier (Grace 4, pore diameter 500 Å, particle size 0.5–1 mm) was washed in 0.2M acetate buffer of pH 4.5 for half an hour and vacuum filtered. 50,000 LU (0.35 g of lipase with an activity of $1.4 \times 10^5$ LU/g) of *Candida antarctica* lipase produced as indicated in EP application No. 87907098.5 was dissolved in 5 ml of deionized water and added to the carrier. The pH value was adjusted to 4.5 and the slurry of carrier and lipase solution was slowly agitated by rotation for 12 hours at room temperature, followed by vacuum filtration. The filtrate contained 19,000 LU corresponding to an adsorption of 62%. The immobilized lipase was air dried and the moisture content adjusted to 10%. The sample was analyzed to 24 BIU/g (60° C. analysis without solvent).

EXAMPLE 3

Hydrolysis With Immobilized Lipase 2.5 g of immobilized lipase produced as indicated in Example 1 in Danish patent application No. 4117/86 (i.e. by means of *Humicola lanuginosa*) at pH 4.5 was added to a flask containing soy bean oil and water and shaken at 50° C. Samples were taken and the free fatty acid content (degree of hydrolysis) was measured by titration with KOH. The experiment was carried out at 25%, 50%, and 75% soy bean oil content. The total amount of oil and water was always 50 g. The results appear from FIG. 3. It appears that the highest degree of hydrolysis is obtained with the highest content of water.

EXAMPLE 4

Ester Synthesis With Immobilized Lipase 0.05 moles (10 g) of lauric acid and 0.05 moles of alcohol was mixed with 5% (w/w) of immobilized lipase, made as described in Example 3. Reaction was carried out at 60° C. by rotating the flask containing the substrate and enzyme. 4 different alcohols were used: lauryl alcohol, pentanol, isopropanol, and propanol. The results appear from FIG. 4. The experiment with lauryl alcohol was carried out under a reduced pressure (approx. 50 mbar). It appears from the figure that the highest conversion is reached with lauryl alcohol and that the enzyme cannot esterify secondary alcohols.

EXAMPLE 5

Continuous Fixed Bed Operation With Immobilized Lipase 2 columns each containing 60 g of immobilized lipase, made as described in Example 3, were packed. The columns were set up in series and the temperature of the columns was 60° C. A similar column system was set up in parallel containing 2 times 60 g of Lipozyme (a commercially available immobilized lipase from Novo-Nordisk A/S) instead. Pure soy bean oil was pumped through the systems and recycled. The bed height of the two systems was measured at time zero. A fixed flow rate was used for 3 days, whereafter the pressure drop over the columns and the bed height of the columns were measured. A new flow rate was then used and the new values were measured after 3 days and so on. The results appear from FIG. 5. It appears from the results that the lipase on a silica carrier is a better enzyme preparation than the commercially available Lipozyme, as the pressure drop is lower for the same flow rate. Further it was observed that there was no compression of the bed containing the silica carrier even after more than 300 hours of operation, whereas the columns containing Lipozyme was compressed up to a total of 13 mm.

EXAMPLE 6

5 g of carrier (Grace 6, pore diameter 1500 Å, particle size 0.5–1 mm) was mixed with a solution containing 250,000 LU of the B component from *Candida antarctica*, as described in WO 88/02775, page 9. The pH value was adjusted to 4.5 and the slurry of carrier and lipase solution was slowly agitated by rotation for 4 hours at room temperature, followed by vacuum drying. The loading of the particles was 28,100 LU/g dry carrier. 125 mg (dry weight) of the immobilized lipase containing approx. 2% water was used for esterification of 40 mmol of propanol and myristic acid at 60° C. Within 20 minutes 29.2% of ester was formed.

EXAMPLE 7

1 g of the silicate carrier Manville R-648 (with average pore diameter 1400 Å) was washed in 0.2M acetate buffer of pH 4.5 for half an hour and vacuum filtered. 186,000 LU (0.06 g of lipase with an activity of $3.1 \times 10^6$ LU/g) of lipase produced as indicated in Example 1 in Danish patent application No. 4117/86, i.e. by means of *Humicola lanuginosa* was dissolved in 5 ml of deionized water and added to the carrier. The pH was adjusted to 4.5 and the slurry of carrier and lipase solution was slowly agitated by rotation for two hours followed by vacuum filtration. The filtrate contained 34,000 LU corresponding to an adsorption of 82%. The immobilized lipase was air dried and the moisture content adjusted to 10%. The sample was analyzed to 14 BIU.

EXAMPLE 8

This example is a comparison example, due to the fact that the pore diameter of the carrier is less than 5 times the diameter of the lipase globules.

1 g of the carrier Amicon Matrex ™ silica Si Chromatography Medium (pore diameter 100 Å, particle size 190–300 μm) was washed in 0.2M acetate buffer of pH 4.5 for half an hour and vacuum filtered. 186,000 LU (0.06 g of lipase with an activity of $3.1 \times 10^6$ LU/g) of lipase (produced as indicated in Example 1 in Danish patent application No. 4117/86) was dissolved in 5 ml of deionized water and added to the carrier. The pH was adjusted to 4.5 and the slurry of carrier and lipase solution was slowly agitated by rotation for two hours followed by vacuum filtration. The filtrate contained 50 LU corresponding to an adsorption of 100%. The immobilized lipase was air dried and the moisture content adjusted to 10%. The sample was analyzed to 6 BIU. The low BIU value indicates that the immobilized lipase is inferior.

We claim:

1. A particulate immobilized microbial lipase consisting essentially of a thermostable lipase isolated from a microorganism selected from the group consisting of a species of the Humicola genus, *Candida antarctica* and *Rhizomucor miehei* and wherein the lipase is adsorbed on particles of a macroporous carrier material, which material consists of at least 65% silica or silicates, wherein an excess of 90% of the particles have particle sizes between 100 and 1000 μm, wherein an excess of 80% of the pores in the particles exhibit a diameter between 12 and 45 times the diameter of a lipase molecule, and wherein the water content of the particulate immobilized lipase is between 1 and 20%.

2. The particulate immobilized lipase according to claim 1, wherein an excess of 90% of the particles have sizes between 200 and 800 μm.

3. The particulate immobilized lipase according to claim 2 wherein an excess of 90% of the particles have sizes between 200 and 400 μm.

4. The particulate immobilized lipase according to claim 1 wherein the water content of the particulate immobilized lipase is between 2 and 20%.

5. The particulate immobilized lipase according to claim 4 wherein the water content of the particulate immobilized lipase is between 5 and 20%.

6. The particulate immobilized lipase according to claim 1, 2, 3, 4, or 5 wherein an excess of 80% of the pores in the particles exhibit a diameter between 12 and 40 times the diameter of the lipase.

7. A method for production of a particulate immobilized lipase consisting essentially of the steps of
   (a) contacting an aqueous solution of a microbial lipase, in which said lipase is a thermostable lipase isolated from a microorganism selected from the group consisting of a species of the Humicola genus, *Candida antarctica* and *Rhizomucor miehei* with particles of a macroporous carrier material, which consists of at least 65% silica or silicates, wherein an excess of 90% of the particles have sizes between 100 and 1000 μm, and wherein an excess of 80% of the pores in the particles exhibit a diameter between 12 and 45 times the diameter of a lipase molecule for a period of time sufficient to adsorb lipase to the carrier material;
   (b) separating the carrier material containing adsorbed lipase in step (a) from the aqueous phase to obtain immobilized lipase; and
   (c) drying the separated immobilized lipase of step (b) to a water content of between 1 and 20%.

8. The method according to claim 7, wherein the proportion between the amount of the aqueous solution of the microbial lipase and the weight of carrier material is 10,000–500,000 LU/g of carrier material by dry weight.

9. The method according to claim 7, wherein the pH during contact between carrier material and aqueous solution does not deviate in an excess of 1 pH unit from optimal loading pH of said lipase in regard to expressed lipase activity.

10. The method according to claim 7 wherein the separation step (b) is performed by filtration.

11. A method for interesterification of fats, comprising contacting liquid fats with a particulate immobilized microbial lipase consisting essentially of a thermostable lipase isolated from a microorganism selected from the group consisting of a species of the Humicola genus, *Candida antarctica* and *Rhizomucor miehei* and wherein the lipase is adsorbed on particles of a macroporous carrier material, which material consists of at least 65% silica or silicates, wherein an excess of 90% of the particles have particle sizes between 100 and 1000 μm, wherein an excess of 80% of the pores in the particles exhibit a diameter between 12 and 45 times the diameter of a lipase molecule, and wherein the water content of the particulate immobilized lipase is between 1 and 20%, said liquid fat being present in an amount to perform said interesterification to produce an interesterified fat.

12. A method for interesterification of fats, comprising contacting a fatty mixture containing a free fatty acid or a fatty acid ester with a particulate immobilized microbial lipase consisting essentially of a thermostable lipase isolated from a microorganism selected from the group consisting of a species of the Humicola genus, *Candida antarctica* and *Rhizomucor miehei* and wherein the lipase is adsorbed on particles of a macroporous carrier material, which material consists of at least 65% silica or silicates, wherein an excess of 90% of the particles have particle sizes between 100 and 1000 μm, wherein an excess of 80% of the pores in the particles exhibit a diameter between 12 and 45 times the diameter of a lipase molecule, and wherein the water content of the particulate immobilized lipase is between 1 and 20%, said fatty mixture being present in an amount to perform said interesterification to produce an interesterified fat.

13. The method according to claim 12 wherein the fatty mixture comprises at least one free fatty acid.

14. The method according to claim 12 wherein the fatty mixture comprises at least one fatty acid ester.

15. A method for the hydrolysis of fats, comprising contacting triglycerides and water with a particulate immobilized microbial lipase consisting essentially of a thermostable lipase isolated from a microorganism selected from the group consisting of a species of the Humicola genus, *Candida antarctica* and *Rhizomucor miehei* and wherein the lipase is adsorbed on particles of a macroporous carrier material, which material consists of at least 65% silica or silicates, wherein an excess of 90% of the particles have particle sizes between 100 and 1000 μm, wherein an excess of 80% of the pores in the particles exhibit a diameter between 12 and 45 times the diameter of a lipase molecule, and wherein the water content of the particulate immobilized lipase is between 1 and 20%, said triglycerides and water being present in an amount effective to perform said hydrolysis to produce a hydrolyzed fat.

16. A method for the synthesis of a fatty acid ester comprising contacting an alcohol and a free fatty acid with a particulate immobilized microbial lipase consisting essentially of a thermostable lipase isolated from a microorganism selected from the group consisting of a species of the Humicola genus, *Candida antarctica* and *Rhizomucor miehei* and wherein the lipase is adsorbed on particles of a macroporous carrier material, which material consists of at least 65% silica or silicates, wherein an excess of 90% of the particles have particle sizes between 100 and 1000 μm, wherein an excess of 80% of the pores in the particles exhibit a diameter between 12 and 45 times the diameter of a lipase molecule, and wherein the water content of the particulate immobilized lipase is between 1 and 20%, said alcohol and said free fatty acid being present in an amount effective to perform said synthesis to produce a fatty acid ester.

17. The method according to claim 16 wherein the fatty acid ester is a glyceride.

18. The method according to claim 17 wherein the alcohol is glycerol or derivative thereof.

* * * * *